United States Patent [19]

Ryan et al.

[11] Patent Number: 4,692,459
[45] Date of Patent: * Sep. 8, 1987

[54] ANTI-HYPERTENSIVE AGENTS

[75] Inventors: James W. Ryan; Alfred Chung, both of Miami, Fla.

[73] Assignee: University of Miami, Coral Gables, Fla.

[*] Notice: The portion of the term of this patent subsequent to Sep. 1, 2004 has been disclaimed.

[21] Appl. No.: 121,188

[22] Filed: Mar. 3, 1980

Related U.S. Application Data

[63] Continuation-in-part of Ser. No. 64,897, Aug. 14, 1979, Ser. No. 64,898, Aug. 14, 1979, Ser. No. 64,899, Aug. 14, 1979, Ser. No. 64,900, Aug. 14, 1979, Ser. No. 64,901, Aug. 14, 1979, Ser. No. 64,902, Aug. 14, 1979, Ser. No. 64,903, Aug. 14, 1979, Ser. No. 116,950, Jan. 30, 1980, abandoned, and Ser. No. 116,951, Jan. 30, 1980, abandoned, said Ser. No. 116,950, is a continuation of Ser. No. 941,289, Sep. 11, 1978, abandoned, said Ser. No. 116,951, is a continuation of Ser. No. 958,180, Nov. 6, 1978, abandoned.

[51] Int. Cl.$^4$ .................... A61K 31/40; A61K 31/41; C07D 207/00; C07D 211/72

[52] U.S. Cl. .................... 514/362; 514/363; 514/255; 514/308; 514/423; 548/531; 548/535; 546/310

[58] Field of Search .................... 424/177; 260/112.5; 548/531, 535; 546/310; 514/362, 363, 255, 308, 423

[56] References Cited

U.S. PATENT DOCUMENTS

| | | | |
|---|---|---|---|
| 3,832,337 | 8/1974 | Ondetti et al. | 260/112.5 R |
| 3,891,616 | 6/1975 | Ondetti et al. | 260/112.5 R |
| 3,947,575 | 3/1976 | Ondetti | 424/177 |
| 4,046,889 | 9/1977 | Ondetti et al. | 424/244 |
| 4,052,511 | 10/1977 | Cushman et al. | 424/274 |
| 4,053,651 | 10/1977 | Ondetti et al. | 424/319 |
| 4,113,715 | 9/1978 | Ondetti | 260/112.5 R |
| 4,154,840 | 5/1979 | Ondetti et al. | 424/267 |

OTHER PUBLICATIONS

Cushman, et al., Experientia, 29,1032 (1973).
Cushman, et al., Biochem., 16, 5484 (1977).
Dorer, et al., Biochem. Biophys. Acta, 429,220 (1976).
Fischer, et al., Ber. 33, 2383 (1900).
Fisher, et al., Arch. Biochem. Biophys., 189 81, (1978).
Fisher, et al., Febs. Letters, 107,273 (1979).
Gavras, et al., New England J. Med. 291, 817 (1974).
Gavras, et al., New Engl. J. Med., 298, 991 (1978).
Lehninger, Biochemistry, Worth Publishers Inc., New York, pp. 153–157 (1970).
Lipmann, Accts Chem. Res. 6,361 (1973).
Ondetti, et al., Science 196, 441 (1977).
Ryan et al., Tissue and Cell, 10, 555 (1978).
Cronyn et al., J. Am. Chem. Soc., 74,4726 (1952).
Lehninger, A., Biochemistry, Worth Publishers, Inc., New York (1975), pp. 189–195.
Ryan, J. W. et al., Biochem. J., 167,501 (1977).
Methoden der Organischen Chem. (Houben–Weyl), vol. XV, Part I, p. 376, et seq. (1974).
Methoden der Organischen Chem. (Houben–Weyl), vol. XV, Part II, p. 1 et seq. (1974).
Carter et al., J. Biol. Chem., 138, 627 (1941).
Engel et al., Proc. Soc. Exp. Biol. Med., 143, 483 (1973).
Jager et al., Chem. Ber., 103,1727 (1970).
Klosterman et al., Biochem 6,170 (1967).
Lijinski et al., Tetrahedron 26,5137 (1970).
Nagasawa et al., J. Med. Chem., 16, 583 (1973).
Pfister et al., J. Am. Chem. Soc., 71,1096 (1941).
Merrifield, Adv. Enzymol 32, 221 (1969).
Ricci et al., Annal. Biochem., 79, 610 (1977).
Oparil et al., Circ. Res. 32, 415 (1973).
Oparil et al., Circ. Res. 29, 682 (1971).
Dorer et al., Biochem J., 141, 915 (1974).
Sharpless, S. K., "Hypnotics and Sedatives", The Pharmacological Basis of Therapeutics, The Macmillan Co. (1965), pp. 105–128.
Buxton et al., J. Chem. Soc., p. 366 (1954).

Primary Examiner—Delbert R. Phillips

[57] ABSTRACT

Inhibitors of angiotensin converting enzyme which have the formula:

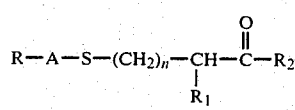

wherein

R is hydrogen, formyl, acetyl propanoyl, butanoyl, phenylacetyl, phenylpropanoyl, benzoyl, cyclopentanecarbonyl, tert-butyloxycarbonyl, cyclopentanecarbonyl-L-lysyl, pyro-L-glutamyl-L-lysyl, L-lysyl, L-arginyl or pyro-L-glutamyl;

A is L-phenylalanyl, D-phenylalanyl, D,L-alanyl, D-alanyl, D,L-tryptophyl, D-tryptophyl, D,L-tyrosyl, D-tyrosyl, D,L-isoleucyl, D-isoleucyl, D,L-leucyl, D-leucyl, D,L-histidyl, D-histidyl, D,L-valyl, or D-valyl, the α-amino group thereof being in amide linkage with R;

$R_1$ is hydrogen or methyl;

$R_2$ is L-proline, L-3,4-dehydroproline, D,L-3,4-dehydroproline, L-3-hydroxyproline, L-4-hydroxyproline, L-thiazolidine-4-carboxylic acid, or L-5-oxoproline, the imino group thereof being in imide linkage with the adjacent

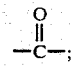

and, n is 0 or 1, such that when n is 0, $R_1$ is methyl are disclosed as useful anti-hypertensive agents.

6 Claims, No Drawings

ANTI-HYPERTENSIVE AGENTS

CROSS REFERENCES TO RELATED APPLICATIONS

This is a continuation-in-part of Ser. Nos. 64,897, 64,898, 64,899, 64,900, 64,901, 64,902 and 64,903, all filed Aug. 14, 1979, Ser. No. 116,950, filed Jan. 30, 1980 which is a continuation of Ser. No. 941,289, filed Sept. 11, 1978, and now abandoned, and Ser. No. 116,951, filed Jan. 30, 1980, now abandoned in favor of its continuation application Ser. No. 295,589 filed Aug. 24, 1981, which is a continuation of Ser. No. 958,180, filed Nov. 6, 1978, and now abandoned, all of which are incorporated herein by reference as though set forth in full. Ser. No. 116,951 has been abandoned in favor of its continuation Ser. No. 295,589, filed Aug. 24, 1981, which has been abandoned in favor of its continuation, Ser. No. 524,204, filed Aug. 18, 1983, which has been abandoned in favor of its continuation, Ser. No. 680,541, filed Dec. 11, 1984, which has been abandoned in favor of its now pending continuation, Ser. No. 850,055, filed Apr. 10, 1986.

BACKGROUND OF THE INVENTION

Angiotensin converting enzyme (peptidyldipeptide hydrolase, hereinafter referred to as ACE) occupies a central role in the physiology of hypertension. The enzyme is capable of converting the decapeptide angiotensin I, having the sequence AspArgValTyrIleHisProPheHisLeu to an octapeptide, angiotensin II by removal of the carboxy-terminal HisLeu. The symbols for various chemical entities have the meaning given in the following table unless otherwise indicated:

Ala=L-alanine
Arg=L-arginine
Asp=L-aspartic acid
Boc=t-butyloxycarbonyl
Glu=glutamic acid
<Glu=pyro-L-glutamic acid (L-5-oxo-proline)
Gly=glycine
Hip=Hippuric acid (Benzoyl glycine)
His=L-histidine
Ile=L-isoleucine
Leu=L-leucine
Phe=L-phenylalanine
Pro=L-proline
ΔPro=L-3,4-dehydroproline
Ser=L-serine
Trp=L-tryptophan
Tyr=L-tyrosine
Val=L-valine
ACE=Angiotensin converting enzyme
Hepes=N-2-hydroxyethylpiperazine-N'-2-ethanesulfonic acid Angiotensin I is formed by the action of the enzyle renin, an endopeptidase found in kidney, other tissues and plasma, acting on a serum α-2 globulin.

Blood pressure is affected by certain peptides found in the blood. One of these, angiotensin II, is a powerful pressor (blood pressure elevating) agent. Another, bradykinin, a nonapeptide with the sequence ArgProProGlyPheSerProPheArg is a powerful depressor (blood pressure lowering) agent. In addition to a direct pressor effect, angiotensin II stimulates release of aldosterone which tends to elevate blood pressure by causing retention of extracellular salt and fluids. Angiotensin II is found in measurable amount in the blood of normal humans. However, it is found at elevated concentrations in the blood of patients with renal hypertension.

The level of ACE activity is ordinarily in excess, in both normal and hypertensive humans, of the amount needed to maintain observed levels of angiotensin II. However it has been found that significant blood pressure lowering is achieved in hypertensive patients by treatment with ACE inhibitors. [Gavras, I., et al., *New Engl. J. Med.* 291, 817 (1974)].

ACE is a peptidyldipeptide hydrolase. It catalyzes the hydrolysis of the penultimate peptide bond at the C-terminal end of a variety of acylated tripeptides and larger polypeptides having an unblocked α-carboxyl group. The action of ACE results in hydrolytic cleavage of the penultimate peptide bond from the carboxyl-terminal end yielding as reaction products a dipeptide and a remnant.

The reactivity of the enzyme varies markedly depending on the substrate. At least one type of peptide bond, having the nitrogen supplied by proline, is not hydrolyzed at all. The apparent Michaelis constant (Km) varies from substrate to substrate over several orders of magnitude. For general discussion of the kinetic parameters of enzyme catalyzed reactions, see Lehninger, A., *Biochemistry*, Worth Publishers, Inc., New York, 1970, pp. 153–157. Many peptides which are called inhibitors of the enzymatic conversion of angiotensin I to angiotensin II are in fact substrates having a lower Km than angiotensin I. Such peptides are more properly termed competitive substrates. Examples of competitive substrates include bradykinin, and the peptide BPP$_{5a}$ (also called SQ20475) from snake venom, whose sequence is <GluLysTrpAlaPro.

Numerous synthetic peptide derivatives have been shown to be ACE inhibitors by Ondetti, et al. in U.S. Pat. No. 3,832,337 issued Aug. 27, 1974.

The role of ACE in the pathogenesis of hypertension has prompted a search for inhibitors of the enzyme that could act as antihypertensive drugs. See for example U.S. Pat. Nos. 3,891,616, 3,947,575, 4,052,511 and 4,053,651. A highly effective inhibitor, with high biological activity when orally administered, is D-3-mercapto-2-methylpropanoyl-L-proline, designated SQ14225, disclosed in U.S. Pat. No. 4,046,889 to Ondetti et al., issued Sept. 6, 1977, and in scientific articles by Cushman, D. W. et al., *Biochemistry* 16, 5484 (1977), and by Ondetti, M. et al., *Science* 196, 441 (1977). The inhibitor SQ14225 reportedly has an I$_{50}$ value of $2.3 \times 10^{-8}$M. The I$_{50}$ value reported by Cushman, et al., supra is the concentration of inhibitor required to produce 50% inhibition of the enzyme under a standard assay system containing substrate at a level substantially above K$_m$. It will be understood that I$_{50}$ values are directly comparable when all potential factors affecting the reaction are kept constant. These factors include the source of enzyme, its purity, the substrate used and its concentration, and the composition of the assay buffer. All I$_{50}$ data reported herein have been performed with the same assay system and same enzyme (human urinary ACE) and with an approximately ½K$_m$ level of substrate and are therefore internally consistent. Discrepancies with data obtained by other workers may be observed. Indeed such discrepancies do exist in the literature, for unknown reasons. See, for example, the $I_{50}$ values for $BPP_{9a}$ reported by Cushman, D. W., et al., *Experientia* 29, 1032 (1973) and by Dorer, F. E., et al., *Biochim.Biophys.Acta* 429, 220 (1976).

The mode of action of SQ 14,225 has been based upon a model of the active site of ACE developed by analogy with the better known related enzyme, carboxypeptidase A. The active site was postulated to have a cationic site for binding the carboxyl end group of the substrate and a pocket or cleft capable of binding the side chain of the C-terminal amino acid and providing especially tight binding for the heterocyclic ring of a terminal proline residue. A similar pocket for the penultimate amino acid residue was postulated, and the published data suggested a rather stringent steric requirement, since the D-form of the inhibitor was substantially more potent than its stereoisomer or the 3-methyl and unsubstituted analogs. The sulfhydryl group on the inhibitor, postulated to be bound at the active site near the catalytic center, was believed to play a central role in inactivation of the enzyme by combining with the zinc moiety known to be essential for catalytic activity. Substituents on the sulfhydryl, such as a methyl group, and an S-acetyl derivative, substantially reduced potency of the inhibitor. See Cushman, D. W., et al., *Biochemistry*, supra.

In vitro study of the mechanism by which SQ 14,225 and its analogs act to inhibit ACE has been somewhat hampered by the instability of these molecules under ambient conditions. For example, it has been observed that a fresh aqueous solution of concentration, e.g., 1 mg per ml of SQ 14,225 at a pH of about 8 becomes substantially less active upon standing for as little as 30 minutes, and that activity continues to decrease as the solution stands for longer periods. It is believed that this loss in activity is mainly the result of dimerization of SQ 14,225 occurring at the sulfhydryl end groups, whereby a disulfide is formed which is largely inactive as an inhibitor. Since the free sulfhydryl group is highly reactive and may be readily oxidized to polar acidic moieties such as sulfone and sulfoxide groups, it may also be that the observed in vitro loss of activity of aqueous solutions of SQ 14,225 on standing is in some part a consequence of one or more such oxidation reactions, with formation of a sulfone or sulfoxide which does not function effectively as an inhibitor for ACE.

Such reports of SQ 14,225 clinical testing as are currently available, some of which refer to the compound under the name "Captopril", suggest that the product is sufficiently stable in the normal gastric and intestinal environments of most patients to be an effective inhibitor for ACE when administered orally. It is not yet clear, however, whether there may be a group of patients for which SQ 14,225 is substantially ineffective. Because of the high reactivity of the free sulfhydryl group, SQ 14,225 could readily form mixed disulfides with serum, cellular proteins, peptides or other free sulfhydryl group-containing substances in the gastric or intestinal environments, in addition to the possibility for dimer formation or oxidative degradation reactions. A mixed disulfide with protein may be antigenic and, indeed, occasional allergic reactions have been clinically observed. See Gavras, et al., *New England J.Med.* 298, 991 (1978). Disulfides and oxidative degradation products of SQ 14,225, if formed, may at best be expected to be largely ineffective as inhibitors. It may be postulated accordingly that dose response to SQ 14,225 may vary with conditions of administration and along individual patients. Moreover, in at least some patients, unwanted side effects may occur and maintenance of an effective concentration of the inhibitor in the body may be difficult to control.

Thioester compounds generally are thought to be highly reactive in that the thioester linkage is readily hydrolyzable to a sulfhydryl moiety and a carboxylic moiety. Thioesters are accordingly often used as active ester intermediates for acylation under mild conditions. See groups as, e.g., acetylthio have been used as blocking groups in the above cited Ondetti, et al. patents. Thioester intermediates are also postulated to occur in the biosynthesis of cyclic peptides such as tyrocidin or gramicidin S. See Lipmann, F. in *Accounts Chem.Res.* 6, 361 (1973).

Thioester compounds having potent ACE inhibitory activity and oral effectiveness as anti-hypertensive agents have been disclosed in copending applications Ser. No. 116,950, filed Jan. 30, 1980, Ser. No. 116,951, filed Jan. 30, 1980, and Ser. Nos. 064,897 through 064,903, all filed on Aug. 14, 1979. All copending applications are incorporated herein by reference.

Compounds related to SQ 14,225 have been disclosed by Ondetti, et al., U.S. Pat. Nos. 4,046,889, 4,052,511, 4,053,651, 4,113,715 and 4,154,840. Of interest are disclosed analogs of SQ 14,225 having the five-membered heterocyclic ring of proline replaced by a four- or a six-membered ring. The inhibitory potencies of such analogs relative to SQ 14,225 are not disclosed. Substitution of D-proline for L-proline is reported to drastically reduce inhibitory potency of 3-mercaptopropanoyl amino acids (Cushman, D. W., et al., supra).

The substitution of L-3,4-dehydroproline for proline has been studied in several systems. Substitution of L-3,4- ΔPro in the 7 position of bradykinin yields a bradykinin derivative which has significantly reduced physiological activity. See Fisher, G. H. et al., *Arch.Biochem.Biophys.* 189, 81 (1978). On the other hand, substitution of L-3,4-ΔPro at the 3, 5, 8 or 9 position in ACE inhibitor $BPP_{9a}$ enhances its inhibitory activity. See Fisher, G. H. et al., *FEBS Letters* 107, 273 (1979). In copending application Ser. No. 958,180, applicants found that the compounds having ΔPro, which are disclosed in said application, have high inhibitory potency and antihypertensive effectiveness. However, at present, no rationale can be advanced to explain the diversity of observed results following substitution of ΔPro for proline. Similarly, no clear picture has emerged of the effects of other proline derivatives or analogs substituted at various loci on ACE inhibitors.

To date, the effect of the amino acid to the left of the sulfur in the thioester compounds disclosed in our copending applications, has not been determined. It is thought that this amino acid functions as an additional recognition site for the enzyme. If this is true, it would be expected that a compound with an amino acid here would be a better inhibitor. Applicants have found that various amino acids are effective and that the hydroxyprolines, proline, L-, and D,L-,3,4-dehydroproline, thiazolidine-4-carboxylic acid, and L-5-oxo-proline derivatives are all effective anti-hypertensive agents and have high inhibitory potency for ACE.

SUMMARY OF THE INVENTION

It was believed when Ser. Nos. 941,289 and 958,180 were filed that N-benzoyl-L-phenylalanine was prepared by the methods disclosed in Examples 4 and 2, respectively, of these applications. Subsequently, it was appreciated from reading *Fischer & Mooneyrat,* Ber, 33, 2383 (1900) that what had actually been prepared by the method described in these examples was the racemized D,L-form of the compound rather than the L- form. It has now been determined that all three optical isomers of the compound N-benzoyl-D,L-phenylalanine, N-benzoyl-L-phenylalanine, and N-benzoyl-D-phenylalanine can be used to prepare compounds which are inhibitors of angiotensin converting enzyme.

It was likewise believed when Ser. Nos. 64,897 through 64,903, inclusive, were filed that all of the amino acids disclosed therein had to be in the L- form in order for the compounds that were prepared to be inhibitors of ACE. It has since been determined that the D- and D,L- forms of these amino acids can also be used to prepare compounds which are ACE inhibitors.

Accordingly, the present invention relates to novel inhibitors of ACE which have the general formula

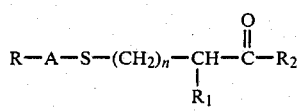

wherein

R is hydrogen, formyl, acetyl, propanoyl, butanoyl, phenylacetyl, phenylpropanoyl, benzoyl, cyclopentanecarbonyl, tert-butyloxycarbonyl, cyclopentanecarbonyl-L-lysyl, pyro-L-glutamyl-L-lysyl, L-lysyl, L-arginyl or pyro-L-glutamyl;

A is L-phenylalanyl, D-phenylalanyl, D,L-alanyl, D-alanyl, D,L-tryptophyl, D-tryptophyl, D,L-tyrosyl, D-tyrosyl, D,L-isoleucyl, D-isoleucyl, D,L-leucyl, D-leucyl, D,L-histidyl, D-histidyl, D,L-valyl, or D-valyl, the α-amino group thereof being in amide linkage with R;

$R_1$ is hydrogen or methyl;

$R_2$ is L-proline, L-3,4-dehydroproline, D,L-3,4-dehydroproline, L-3-hydroxyproline, L-4-hydroxyproline, L-thiazolidine-4-carboxylic acid, or L-5-oxoproline, the imino group thereof being in imide linkage with the adjacent

and, n is 0 or 1, such that when n is 0, $R_1$ is methyl.

All of the above compounds are inhibitors of ACE and are useful as orally effective anti-hypertensive agents.

DESCRIPTION OF THE PREFERRED EMBODIMENTS

A more complete appreciation of the invention will be realized by reference to the following specific examples which describe the details of the synthesis and operational effectiveness of the foregoing compounds. The following examples are not intended to limit the invention disclosed herein except to the extent that limitations are specifically stated or to the extent to which limitations appear in the appended claims.

EXAMPLE 1

ACE activity assay. For most experiments described herein, the enzyme was assayed in 0.05M Hepes buffer, pH 8.0 containing 0.1M NaCl and 0.75M $Na_2SO_4$. The substrate employed was Benzoyl-GlyHisLeu at a final concentration of $1 \times 10^{-4}$M, ($Km \approx 2 \times 10^{-4}$M), together with about 130,000 cpm of [$^3$H]BenzoylGlyHis-Leu (25 Ci/mmole). Enzyme was diluted in the above buffer such that 40 μl buffered enzyme was capable of hydrolyzing 13% of substrate in a 15-minute incubation at 37° C. To initiate the assay, 40 μl of enzyme and 10 μl of buffer or inhibitor dissolved in buffer were preincubated for five minutes at 37° C. Substrate, 50 μl was then added to initiate reaction and the solution was incubated for 15 minutes at 37° C. To terminate the reaction, 1 ml of 0.1M HCl was added, following which 1 ml of ethyl acetate was added. The mixture was agitated on a rotary mixer and centrifuged briefly to separate the phases.

An aliquot, 500 μl, of the ethyl acetate layer was transferred to a liquid scintillation vial containing 10 ml of Riafluor, trademark New England Nuclear Corporation, Boston, Massachusetts. For determination of $I_{50}$ values, enzyme activity in the presence of inhibitor at a series of different concentrations was compared to activity in the absence of inhibitor. A plot of inhibitor concentration versus percent inhibition yielded the $I_{50}$ value.

EXAMPLE 2

Preparation of N-[3-(benzoyl-L-phenylalanylthio)-2-D-methylpropanoyl]-L-proline a. Preparation of N-[3-(Boc-L-phenylalanylthio)-2-D-methylpropanoyl]-L-proline A solution of 133 mg (0.5 mmole) of Boc-L-Phe-OH in 0.5 ml of redistilled dimethylformamide (DMF) was cooled to −20° C. in an ice-dry ice-acetone bath. A cooled solution of 87 mg (0.54 mmole) of 1,1'-carbonyldiimidazole in 1 ml of DMF was added and the resulting solution was stirred at −10° C. for 2 h. DMF, 1.0 ml, containing 119.5 mg (0.55 mmole) of 2-D-methyl- 3-mercaptopropanoyl-L-proline and 0.075 ml (0.55 mmole) of N-ethylmorpholine, all at −10° C., was added, and the final solution was stirred at −10° C. for 1 h. The reaction mixture was slowly warmed to room temperature. Solvent was removed with a rotary evaporator. Ethyl acetate (10 ml) was added and the solution was cooled in an ice bath. The organic solution was washed twice with about 2 ml of 1N citric acid and then was washed twice with a saturated NaCl solution. The ethyl acetate phase was dried over anhydrous $MgSO_4$ and then filtered. The solvent of the filtrate was removed with a rotary evaporator. The residue was dissolved in a small volume of isopropanol/tetrahydrofuran (7:3 by vol) and was applied to a column (1.2×99 cm) of Sephadex LH-20 equilibrated with the same solvent. Each column eluent fraction contained 2.55 ml. Fractions 31–36 were pooled, and solvent was removed by rotary evaporation. The residue was again dissolved in the isopropanoyl/tetrahydrofuran solvent and was applied to a column (1.2×98 cm) of Sephadex G-10 equilibrated and developed with the same solvent. Fractions, 2.55 ml each, were collected. Fractions 19–23 were pooled and yielded 165 mg of the desired product. Purification of side fractions from the LH-20 chromatography step yielded 40 mg of product. The product behaved as a pure substance on paper electrophoresis at pH 5.0 and on thin layer chromatography (silica gel plates) using three solvent systems. Amino acid analysis: $^{Phe}1.00$, $^{Pro}1.01$.

b. Preparation of N-[3-(HCl.H-L-phenylalanylthio)-2-D-methyl-propanoyl]-L-proline Anisole (0.2 ml) was added to 200 mg of N-[3-(Boc-L-phenylalanylthio)-2-D-methyl-propanoyl-L-proline, and the mixture was stirred at 0° C. Anhydrous trifluoroacetic acid (0.4 ml) was added, and the solution was stirred at room temperature (~22° C.) for 45 min. Trifluoroacetic acid was removed by rotary evaporation at 30° C. and then 1 ml of ethyl acetate saturated with hydrogen chloride was added. Excess HCl and ethyl acetate were removed with a rotary evaporator to yield an oily residue. Anhydrous ethyl ether was added, and the mixture was allowed to stand at 0° C. for 1 h. A white solid was recovered by filtration and washed several times with anhydrous ether. The solid material was dried in a vacuum desiccator over NaOH and $P_2O_5$.

c. Preparation of N-[3-(benzoyl-L-phenylalanylthio)-2-D-methyl-propanoyl]-L-proline A solution of 93 mg (0.23 mmole) of N-[3-(HCl.H-L-phenylalanylthio)-2-D-methyl-propanoyl]-L-proline in 0.5 ml of dioxane (redistilled over Na) was mixed with 0.029 ml (0.25 mmole) of benzoylchloride in 0.099 ml (0.71 mmole) of N-ethyl morpholine. After 1 h of reaction at room temperature, an additional 0.029 ml of benzoylchloride and 0.034 ml of N-ethyl morpholine were added. One h after the second addition, glacial acetic acid (0.2 ml) was added. Solvent was removed by rotary evaporation at 35° C. The crude product was purified by partition chromatography [1.2×97 cm column of Sephadex G-25 equilibrated with n-butanol/acetic acid/$H_2O$ (4:1:5)]. The sample was dissolved in a mixture of 0 3 ml of lower phase and 0.3 ml of upper phase. Elution was begun with upper phase. Fractions (2.75 ml each) were collected. Fractions 16-18 were pooled, and solvent was removed at 37° C. with a rotary evaporator. The product was then applied to a column (1.2×98 cm) of silica gel equilibrated and developed with ethyl acetate. Fractions (5.15 ml each) were collected. Fractions 46-60 were pooled and yielded 52.5 mg of product. The product behaved like a pure substance on thin layer chromatography using two solvent systems.

EXAMPLE 3

Preparation of N-[3-(benzoyl-D-phenylalanylthio)-2-D-methyl-propanoyl-L-proline a. Preparation of N-[3-(HCl.H-D-phenylalanylthio)-2-D-methyl-propanoyl-L-proline A solution of 531 mg (2 mmoles) of Boc-D-phenylalanine in 3 ml of redistilled dimethylformamide (DMF) was cooled to −20° C. and stirred vigorously. 1,1'-carbonyldiimidazole (341 mg; 2.1 mmole) in 3 ml of DMF (at −10° C.) was added, and the resulting solution was stirred at −10° for 2 h. A solution of 2-D-methyl-3-mercaptopropanoyl-L-proline (456 mg; 2.1 mmole) in 2 ml of DMF and 0.285 ml of N-ethyl morpholine (2.1 mmole) was added, and the reaction mixture was stirred at −10° C. for 1 h. The mixture was slowly warmed to room temperature. Solvent was removed by rotary evaporation at 35° C. The residue was dissolved in ethyl acetate (25 ml) and 3 ml of water was added. The mixture was cooled to 0° C. and then acidified with 0.3 ml of concentrated HCl. The organic phase was washed once with cold dilute HCl, three times with water, and three times with saturated NaCl. The organic phase was dried over anhydrous $MgSO_4$ and then was filtered. The solvent was removed by rotary evaporation to yield an oily residue. The product was purified on a column (2.2×98 cm) of Sephadex LH-20 equilibrated and developed with isopropanol/tetrahydrofuran (7:3 by vol). Fractions (5.6 ml each) were collected. Fractions 34-38 were pooled. Fractions 33, 39, 40 and 41 were pooled, solvents removed and reapplied to the LH-20 column. Fractions 37-40 of the rechromatographed material and fractions 34-38 of the first chromatography were further purified on a column (1.2×98 cm) of silica gel equilibrated and developed with ethyl acetate. Fractions (5.0 ml each) were collected. Fractions 22-29 were pooled, and solvent was removed by rotary evaporation. The residue was dissolved in 1 ml of anhydrous trifluoroacetic acid containing 0.5 ml of anisole. Deprotection proceeded at room temperature for 0.5 h. Solvent was removed by rotary evaporation at 35° C. The residue was dissolved in 1 ml of ethyl acetate saturated with hydrogen chloride. Anhydrous ether, 5 ml, was added at 0° C., and a white precipitate formed. After 1 h at 0° C., the white solid was collected by filtration and was washed five times with ether. The product was dried overnight in a vacuum desiccator over NaOH and $P_2O_5$ Yield: 381 mg.

b. Preparation of N-[3-(benzoyl-D-phenylalanylthio)-2-D-methyl-propanoyl]-L-proline The product of stage a. above, N-[3-(HCl.H-D-phenylalanyl-thio)-2-D-methyl-propanoyl]-L-proline (93 mg; 0.23 mmole), was reacted with benzoylchloride (0.029 ml; 0.25 mmole) in 0.5 ml of redistilled anhydrous dioxane (0° C.) and 0.099 ml (0.71 mmole) of N-ethyl morpholine. The reaction mixture was stirred vigorously at room temperature for 3 h. Benzoylchloride, 0.015 ml, and N-ethyl morpholine, 0.018 ml. were added and the mixture was stirred for 1 h. Solvent was removed by rotary evaporation at 30° C. The residue was dissolved in a small amount of upper and lower phase of n-butanol/acetic acid/H20 (4:1:5) and was applied to a column (1.2×98 cm) of Sephadex G-25 equilibrated for partition chromatography. The column was developed with upper phase as the moving phase (2.6 ml fractions). Fractions 15-24 were pooled and solvent removed by rotary evaporation. The residue was dissolved in a small amount of ethyl acetate and further purified on silica gel (1.2×95 cm column) equilibrated and developed with ethyl acetate (5 ml fractions). The fractions containing the major peak were pooled and solvent was removed. The material was further purified by chromatography on Sephadex LH-20 (1.8× 89 cm column) equilibrated and developed with isopropanol/tetrahydrofuran (7:3 by vol). Fractions (5.7 ml each) were collected, and the desired material was eluted in fractions 15-18 (yield 98 mg). The final product behaved as a pure substance on paper electrophoresis at pH 5.0 and 2.0 and on thin layer chromatography.

EXAMPLE 4

Preparation of
N-[3-(benzoyl-D,L-phenylalanylthio)-2-D-methyl-propanoyl]-L-proline By using a 50:50 mixture of Boc-D-phenylalanine and Boc-L-phenylalanine in the procedures of Example 2 or 3 above, N-[3-(benzoyl-D,L-phenylalanylthio)-2-D-methyl-propanoyl]-L-proline is prepared.

EXAMPLE 5

Preparation of
N-(2-benzoylphenylalanylthiopropanoyl)-L-proline
and
N-(3-benzoylphenylalanylthiopropanoyl)-L-proline derivatives The desired compound is prepared by substituting either 2-mercaptopropanoyl-L-proline or 3-mercaptopropanoyl-L-proline for 2-D-methyl-3-mercaptopropanoyl-L-proline in the procedures of Examples 2-4 above, and reacting the mercapto compound with either Boc-D-phenylalanine, Boc-L-phenylalanine, or a 50:50 mixture thereof.

The mercapto compounds can be prepared using the procedures described in any of the applications of which this application is a continuation-in-part, which are incorporated herein by reference.

EXAMPLE 6

Preparation of L-3,4-dehydroproline,
D,L-3,4-dehydroproline, L-3-hydroxyproline,
L-4-hydroxyproline and L-thiazolidine-4carboxylic acid derivatives The desired compound is prepared by using the appropriate mercapto compound in which L-3,4-dehydroproline, D,L-3,4dehydroproline, L-3-hydroxyproline, L-4-hydroxyproline or L-thiazolidine-4-carboxylic acid is substituted for L-proline in the procedures of Example 2-5 above.

The appropriate mercapto compounds can be prepared using the procedures described in Ser. Nos. 64,897 to 64,903, incorporated herein by reference.

EXAMPLE 7

Preparation of D-alanyl, D-tryptophyl, D-tyrosyl, Disoleucyl, D-leucyl, D-histidyl and D-valyl derivatives The desired compound is prepared by substituting Boc-D-alanine, Boc-D-tryptophan, Boc-D-tyrosine, Boc-D-isoleucine, Boc-D-leucine, Boc-D-histidine or Boc-D-valine for Boc-D-phenylalanine in the procedures of Examples 2, 5 and 6 above.

EXAMPLE 8

Preparation of D,L-alanyl, D,L-tryptophyl,
D,L-tyrosyl, D,L-isoleucyl, D,L-leucyl, D,L-histidyl and D,L-valyl derivatives A 50:50 mixture of Boc-D-A and Boc-L-A, wherein A is alanine, tryptophan, tyrosine, isoleucine, leucine, histidine or valine, is substituted for the mixture of Boc-D-phenylalanine and Boc-L-phenylalanine in the procedures of Examples 4-6 above to obtain the desired compounds.

EXAMPLE 9

By substituting the appropriate compound for benzoyl chloride in Examples 2, 3 and 5-8 above and following procedures well known in the art, such as those described in Ser. Nos. 64,897 to 64,903, the formyl, acetyl, propanoyl, butanoyl, phenylacetate, phenylpropanoyl, cyclopentanecarbonyl, cyclopentanecarbonyl-L-lysyl, pyro-L-glutamyl-L-lysyl, L-lysyl, L-arginyl and pyro-L-glutamyl derivatives are prepared.

EXAMPLE 10

Preparation of
N-[3-(benzoyl-L-phenylalanylthio)-2-methyl-propanoyl]-L-5-oxo-proline L-glutamic acid, 10 mmoles is reacted with 11 mmoles of the acid chloride of methacrylic acid in 35 ml of 1N sodium hydroxide. After 60 min. at room temperature, the reaction is terminated by adding 2N HCl to a pH of ~2. The reaction product is extracted twice with an equal volume of ethyl acetate. The organic phase is reduced to a small volume on a rotary evaporator, and the product is crystallized by adding ethyl ether. The solid product is collected by filtration. Six mmoles of the product are reacted with 6 mmoles of cyclohexylcarbodiimide in 25 ml of anhydrous tetrahydrofuran at 0° C. for 1 h and then at 4° C. overnight. The dicyclohexylurea is removed by filtration. The solvent of the filtrate is removed with a rotary evaporator. The resulting anhydride (5 mmoles) is dissolved in 3 ml of anhydrous THF and 6 ml of anhydrous ethyl ether. To the latter solution is added dicyclohexylamine, 5 mmoles in 2 ml of ethyl ether, to yield methacryloyl-L-5-oxo-proline. The salt is converted to the free acid by adding 2N HCl to pH 2.0. The product is extracted into ethyl acetate. The organic phase is evaporated to dryness and the product is crystallized from a mixture of hexane and ethyl acetate. The methacryloyl-L-5-oxo-proline, 3 mmoles in 5 ml of toluene, is reacted with thiolacetic acid, 3 mmoles, by refluxing for 1 h to yield 3-acetylthio-2-methyl-propanoyl-L-oxo-proline. The product is crystallized in a mixture of ethyl acetate and hexane. The 3-acetylthio-2-methyl-propanoyl-L-5-oxo-proline is deprotected in liquid $NH_3$ in methanol in the presence of anisole. Solvent is removed with a rotary evaporator. The product is dissolved in ethyl acetate and the organic phase is washed with cold dilute HCl. The solvent of the organic phase is removed with a rotary evaporator. The residue is dissoved in dimethylformamide, 4 ml. 1-Hydroxybenzotriazole, 2 mmoles, and the N-hydroxy-succinimide ester of benzoyl-L-phenylalanine, 2 mmoles, are added. The reaction is allowed to proceed at room temperature for 48 h. The solvent is removed with a rotary evaporator. The residue is dissolved in a small volume of ethyl acetate. The organic phase is washed with cold dilute HCl and then saturated NaCl. The organic phase is dried over $MgSO_4$. The $MgSO_4$ is removed by filtration and solvent of the filtrate is removed with a rotary evaporator. The residue is dissolved in 0.5 ml of THF. The resulting solution is applied to a column (2.5 × 100 cm) of LH-20 equilibrated and developed with THF. The fractions containing the desired product (detectable by its absorption at 280 nm) are combined, and solvent is removed in a rotary evaporator under high vacuum.

EXAMPLE 11

The inhibitory potency of various of the above-synthesized compounds in vitro was measured in the assay system described in Example 1. The enzyme preparation was purified from human urine as described by Ryan, J. W., et al., *Tissue and Cell* 10, 555 (1978). Table 1 shows the $I_{50}$ value for various compounds. The $I_{50}$ value is the concentration of inhibitor required to produce 50% inhibition of the enzyme under a standard assay system containing substrate at a level substantially below $K_m$.

TABLE 1

| Compound | $I_{50}$ |
| --- | --- |
| Example 2 | $1.6 \times 10^{-8}$ M |
| Example 3 | $9 \times 10^{-9}$ M |

What is claimed is:

1. A new compound having the formula:

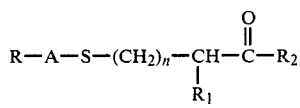

wherein

R is hydrogen, formyl, acetyl, propanoyl, butanoyl, phenylacetyl, phenylpropanoyl, benzoyl, cyclopentanecarbonyl, tert-butyloxycarbonyl, cyclopentanecarbonyl-L-lysyl, pyro-L-glutamyl-L-lysyl, L-lysyl, L-arginyl or pyro-L-glutamyl;

A is D-phenylalanyl, D,L-alanyl, D-alanyl, D,L-tryptophyl, D-tryptophyl, D,L-tyrosyl, D-tyrosyl, D,L-isoleucyl, D-isoleucyl, D,L-leucyl, D-leucyl, D,L-histidyl, D-histidyl, D,L-valyl, or D-valyl, the α-amino group thereof being in amide linkage with R unless R is hydrogen; when R is not hydrogen, it being understood that when R is benzoyl and $R_2$ is a residue of L-proline or a dehydroproline, A may also be L-phenylalanyl $R_1$ is hydrogen or methyl;

$R_2$ is a residue of L-proline, L-3,4-dehydroproline, D,L-3,4dehydroproline, L-3-hydroxyproline, L-4-hydroxyproline, L-thiazolidine-4-carboxylic acid, or L-5-oxo-proline, the imino group thereof being in imide linkage with the adjacent

and, n is 0 or 1, such that when n is 0, $R_1$ is methyl.

2. A compound of claim 1 wherein R is benzoyl, A is D-phenylalanyl or L-phenylalanyl, $R_1$ is methyl, $R_2$ is a residue of L-proline and n is 1.

3. A compound of claim 1 wherein R is hydrogen, A is L-phenylalanyl, $R_1$ is methyl, $R_2$ is a residue of L-proline and n is 1.

4. A compound of claim 1 wherein R is hydrogen, A is D-phenylalanyl, $R_1$ is methyl, $R_2$ is a residue of L-proline and n is 1.

5. A method for inhibiting angiotensin converting enzyme Z in vivo comprising administering an effective oral dose of an inhibitor of claim 1.

6. A method for reducing blood pressure in vivo comprising administering an effective oral dose of an inhibitor of claim 1.

* * * * *

UNITED STATES PATENT AND TRADEMARK OFFICE
CERTIFICATE OF CORRECTION

PATENT NO. : 4,692,459

DATED : September 8, 1987

INVENTOR(S) : James W. Ryan and Alfred Chung

It is certified that error appears in the above-identified patent and that said Letters Patent is hereby corrected as shown below:

Col 3, line 68 "along" should read "among"

Col 7, line 4 "HCl.H" should read "HCl·H"

Col 7, line 24 "HCl.H" should read "HCl·H"

Col 7, line 55 "HCl.H" should read "HCl·H"

Col 7, line 62, add "C" after "-10°" so that it reads "-10°C"

Col 8, line 32, add a period (.) after "$P_2O_5$" so that it reads "$P_2O_5$."

Col 8, line 38 "HCl.H" should read "HCl·H"

Col 8, line 50 "H20" should read "$H_2O$"

Col 9, line 34, add a hyphen (-) after "-4" so that it reads "-4-carboxylic"

Col 9, line 39, add a hyphen - after "D,L-3,4" so that it reads "D,L -3,4-dehydro"

Col 10, line 43, add "5-" after "L-" and before "oxo" so that it reads "L-5-oxo"

Col 10, line 52, add a space after "4ml." and before "1-" so that it reads "4ml. 1-"

UNITED STATES PATENT AND TRADEMARK OFFICE
CERTIFICATE OF CORRECTION

PATENT NO. : 4,692,459

DATED : September 8, 1987

INVENTOR(S) : James W. Ryan and Alfred Chung

It is certified that error appears in the above-identified patent and that said Letters Patent is hereby corrected as shown below:

Col 12, line 30, delete the "Z" after "enzyme z" so that it reads "enzyme"

Signed and Sealed this

Twenty-seventh Day of September, 1988

Attest:

DONALD J. QUIGG

Attesting Officer

Commissioner of Patents and Trademarks